United States Patent
Nampoothiri K. et al.

(10) Patent No.: US 6,638,753 B2
(45) Date of Patent: Oct. 28, 2003

(54) NUCLEOTIDE SEQUENCES WHICH CODE FOR THE CMA GENE

(75) Inventors: Madhavan Nampoothiri K., Kerala (IN); Bettina Möckel, Düsseldorf (DE); Lothar Eggeling, Jülich (DE); Hermann Sahm, Jülich (DE)

(73) Assignees: Degussa AG, Düsseldorf (DE); Forschungszentrum Julich GmbH, Julich (DE)

( * ) Notice: Subject to any disclaimer, the term of this patent is extended or adjusted under 35 U.S.C. 154(b) by 0 days.

(21) Appl. No.: 09/845,248

(22) Filed: May 1, 2001

(65) Prior Publication Data

US 2002/0042106 A1 Apr. 11, 2002

Related U.S. Application Data

(63) Continuation-in-part of application No. 09/577,857, filed on May 25, 2000, now abandoned.

(30) Foreign Application Priority Data

May 4, 2000 (DE) .......................... 100 21 832

(51) Int. Cl.[7] .............. C12N 9/10; C12N 1/20; C12N 15/00; C07H 21/02; C07H 21/04

(52) U.S. Cl. ............... 435/252.3; 435/252.32; 435/320.1; 435/193; 536/23.1; 536/24.3

(58) Field of Search ............. 435/252.32, 193, 435/320.1; 536/23.2, 23.1, 24.32, 24.3

(56) References Cited

U.S. PATENT DOCUMENTS 6,441,151 B1 * 8/2002 Gordon-Kamm et al. .. 536/23.1

OTHER PUBLICATIONS

Pub. No. US202/0197605 A1, Nakagawa S. et al, Novel polynucleotides, Dec. 26, 2002.*
Sulton J. E. et al. Toward a Complete Human Genome Sequence, Genome Research, 1998, 8/11, 1097–1108.*

* cited by examiner

Primary Examiner—Rebecca E. Prouty
Assistant Examiner—Malgorzata Walicka
(74) Attorney, Agent, or Firm—Smith, Gambrell & Russell

(57) ABSTRACT

The invention relates to a genetically modified coryneform bacterium, the cma gene of which is amplified, and an isolated polynucleotide which codes for cyclopropane-mycolic acid synthase from coryneform bacteria, and also a method for the fermentative preparation of L-amino acids with amplification of the cma gene in the bacteria and the use of the polynucleotide as a primer or hydridization probe.

21 Claims, 1 Drawing Sheet

Figure 1: Plasmid map pJC1cma
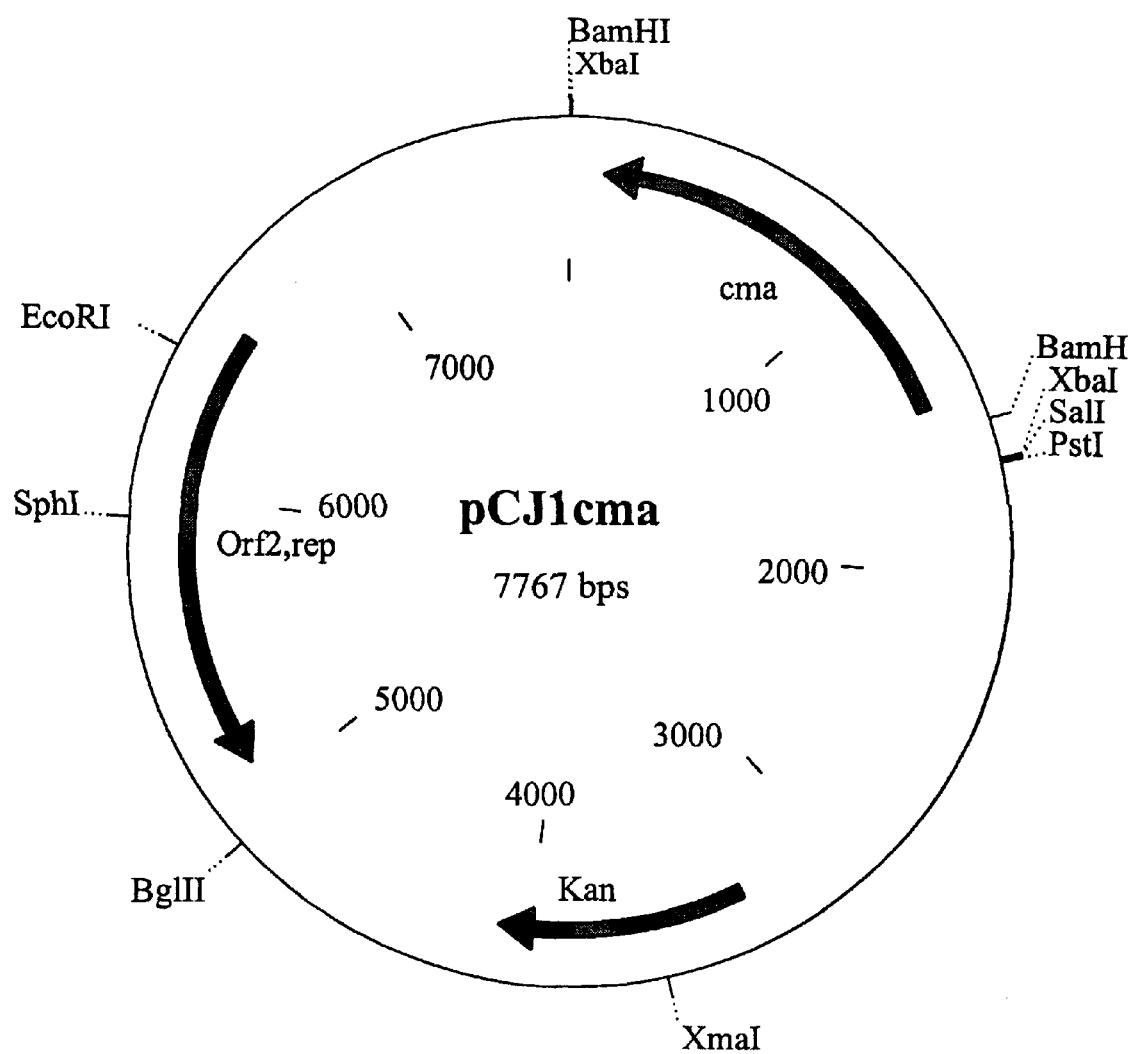

US 6,638,753 B2

NUCLEOTIDE SEQUENCES WHICH CODE FOR THE CMA GENE

RELATED APPLICATION DATA

This application is a Continuation-in-Part of U.S. patent appln. Ser. No. 09/577,857 filed May 25, 2000, now abandoned, which application claims priority under 35 U.S.C. §119 from German Patent Appln. No. 10021832.6, filed in Germany on May 4, 2000. The above-identified U.S. patent application and German patent application are entirely incorporated herein by reference.

The invention provides genetically modified coryneform bacteria, nucleotide sequences which code for cyclopropane-mycolic acid synthase and a method for the fermentative preparation of amino acids, in particular L-lysine and L-glutamate, using coryneform bacteria in which the cma gene, which codes for cyclopropane-mycolic acid synthase, is amplified. All references cited herein are expressly incorporated by reference. Incorporation by reference is also designated by the term "I.B.R." following any citation.

PRIOR ART

Amino acids, in particular L-lysine and L-glutamate, are used in human medicine, in the pharmaceuticals industry, in the foodstuffs industry, but in particular in animal nutrition.

It is known that amino acids are produced by fermentation from strains of coryneform bacteria, in particular *Corynebacterium glutamicum*. Because of their great importance, work is constantly being undertaken to improve the preparation methods. Improvements to the methods can relate to fermentation measures, such as e. g. stirring and supply of oxygen, or the composition of the nutrient media, such as e. g. the sugar concentration during the fermentation, or the working up to the product form by e.g. ion exchange chromatography, or the intrinsic output properties of the microorganism itself.

Methods of mutagenesis, selection and mutant selection are used to improve the output properties of these microorganisms. Strains which are resistant to antimetabolites, such as e.g. the lysine analogue S-(2-aminoethyl)-cysteine, or are auxotrophic for metabolites of regulatory importance and produce L-amino acids, such as e. g. L-lysine or L-glutamate, are obtained in this manner.

Methods of the recombinant DNA technique have also been employed for some years for improving the strain of Corynebacterium strains which produce amino acids, by amplifying individual amino acid biosynthesis genes and investigating the effect on the amino acid production. Review articles in this context are to be found, inter alia, in Kinoshita ("Glutamic Acid Bacteria", in: Biology of Industrial Microorganisms, Demain and Solomon (Eds.) I.B.R., Benjamin Cummings, London, UK, 1985, 115–142), Hilliger (BioTec 2, 40–44 (1991)) I.B.R., Eggeling (Amino Acids 6:261–272 (1994)) I.B.R., Jetten and Sinskey (Critical Reviews in Biotechnology 15, 73–103 (1995)) I.B.R. and Sahm et al. (Annuals of the New York Academy of Science 782, 25–39 (1996)) I.B.R.

OBJECT OF THE INVENTION

The object of the present invention was to provide new aids for improved fermentative preparation of amino acids, in particular L-lysine and L-glutamate.

This object is achieved by a genetically modified coryneform bacterium, the cma gene of which, which codes for cyclopropane-mycolic acid synthase, is amplified.

Amino acids, in particular L-lysine and L-glutamate, are used in human medicine, in the pharmaceuticals industry, in the foodstuffs industry, and in particular in animal nutrition. There is therefore a general interest in providing new improved methods for the preparation of amino acids, in particular L-lysine and L-glutamate.

When L-lysine or lysine and L-glutamate or glutamate are mentioned in the following, not only the bases but also the salts, such as e. g. lysine monohydrochloride or lysine sulfate, are also meant by this.

SUMMARY OF THE INVENTION

The new DNA sequence of *C. glutamicum* which codes for the cma gene and which as a constituent of the present invention is SEQ ID NO 1 and related sequences. The amino acid sequence of the corresponding gene product of the cma gene has furthermore been derived from the present DNA sequence. The resulting amino acid sequence of the cma gene product is SEQ ID NO 2 and related sequences.

BRIEF DESCRIPTION OF THE DRAWINGS

The present invention will be further understood with reference to the drawing offered here for illustration only and not in limitation of this invention.

FIG. 1: Map of the plasmid pJC1cma

DETAILED DESCRIPTION OF THE INVENTION

The invention provides a genetically modified coryneform bacterium, in which its cma gene, which codes for cyclopropane-mycolic acid synthase, is amplified.

The term "amplification" in this connection describes the increase in intracellular activity of one or more enzymes in a microorganism which are coded by the corresponding DNA.

Amplification can be achieved with the aid of various manipulations of the bacterial cell.

To achieve an amplification, in particular an overexpression, the number of copies of the corresponding genes can be increased, a potent promoter can be used, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative L-lysine or L-glutamate production. It is also possible to use a gene which codes for a corresponding enzyme with a high activity. The expression is likewise improved by measures to prolong the life of the m-RNA. Furthermore, the enzyme activity is also increased overall by preventing the degradation of the enzyme. These measures can optionally also be combined as desired.

The microorganisms which the present invention provides can prepare L-amino acids, in particular L-lysine and L-glutamate, from glucose, sucrose, lactose, fructose, maltose, molasses, starch, cellulose or from glycerol and ethanol. They can be representatives of coryneform bacteria, in particular of the genus Corynebacterium. Of the genus Corynebacterium, there may be mentioned in particular the species *Corynebacterium glutamicum*, which is known among experts for its ability to produce L-amino acids.

Suitable strains of the genus Corynebacterium, in particular of the species *Corynebacterium glutamicum*, are, for example, the known wild-type strains

*Corynebacterium glutamicum* ATCC13032
*Corynebacterium acetoglutamicum* ATCC15806

*Corynebacterium acetoacidophilum* ATCC13870
*Corynebacterium thermoaminogenes* FERM BP-1539
*Corynebacterium melassecola* ATCC17965
*Brevibacterium flavum* ATCC14067
*Brevibacterium lactofermentum* ATCC13869 and
*Brevibacterium divaricatum* ATCC14020
and L-lysine-producing mutants or strains prepared therefrom, such as, for example
*Corynebacterium glutamicum* FERM-P 1709
*Brevibacterium flavum* FERM-P 1708
*Brevibacterium lactofermentum* FERM-P 1712
*Corynebacterium glutamicum* FERM-P 6463
*Corynebacterium glutamicum* FERM-P 6464 and
*Corynebacterium glutamicum* DSM5715.

The present invention also provides an isolated polynucleotide from coryneform bacteria, comprising a polynucleotide sequence chosen from the group consisting of
a) polynucleotide which is homologous to the extent of at least 70% with a polynucleotide which codes for a polypeptide which comprises the amino acid sequence of SEQ ID No. 2,
b) polynucleotide which codes for a polypeptide which comprises an amino acid sequence which is homologous to the extent of at least 70% with the amino acid sequence of SEQ ID No. 2,
c) polynucleotide which is complementary to the polynucleotides of a) or b), and
d) polynucleotide comprising at least 15 successive nucleotides of the polynucleotide sequence of a), b) or c).

In the context of the present Application, a polynucleotide sequence is "homologous" to the sequence according to the invention if it coincides in its base composition and sequence with the sequence according to the invention to the extent of at least 70%, preferably at least 80%, particularly preferably at least 90%. According to the present invention, a "homologous protein" is to be understood as proteins which have an amino acid sequence which coincide with the amino acid sequence coded by the cma gene (SEQ ID No. 1) to the extent of at least 70%, preferably at least 80%, particularly preferably at least 90%, "coincide" being understood as meaning that either the corresponding amino acids are identical or they are amino acids which are homologous to one another. Those amino acids which correspond in their properties, in particular in respect of charge, hydrophobicity, steric properties etc., are called "homologous amino acids".

The invention also provides a polynucleotide as described above, this preferably being a DNA which is capable of replication, comprising:
(i) the nucleotide sequence shown in SEQ ID NO. 1, or
(ii) at least one sequence which corresponds to sequence (i) in the context of the degeneration of the genetic code, or
(iii) at least one sequence which hybridizes with the sequence complementary to sequence (i) or (ii), and optionally
(iv) mutations of neutral function in (i) which lead to the same or a homologous amino acid.

The relative degree of substitution or mutation in the polynucleotide or amino acid sequence to produce a desired percentage of sequence identity can be established or determined by well-known methods of sequence analysis. These methods are disclosed and demonstrated in Bishop, et al. "DNA & Protein Sequence Analysis (A Practical Approach"), Oxford Univ. Press, Inc. (1997) *I.B.R.* and by Steinberg, Michael "Protein Structure Prediction" (A Practical Approach), Oxford Univ. Press, Inc. (1997) *I.B.R.*

Hybridization of complementary sequences can occur at varying degrees of stringency. Sambrook et al.: Molecular Cloning, A Laboratory Manual (Cold Spring Harbor Laboratory Press, 1989) *I.B.R.*

Hybridization of complementary sequences can occur at varying degrees of stringency. Sambrook et al.: Molecular Cloning, A Laboratory Manual (Cold Spring Harbor Laboratory Press, 1989) *I.B.R.* Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) *I.B.R.* and in Liebl et al. (International Journal of Systematic Bacteriology (1991) 41: 255–260) *I.B.R.*

Comprehensive descriptions can be found in known textbooks of genetics and molecular biology, such as e.g. that by Hagemann ("Allgemeine Genetik" [General Genetics], Gustav Fischer Verlag, Stuttgart, 1986) *I.B.R.*

Possible mutations are transitions, transversions, insertions and deletions. Depending on the effect of the amino acid exchange on the enzyme activity, missense mutations or nonsense mutations are referred to. Insertions or deletions of at least one base pair in a gene lead to frame shift mutations, as a consequence of which incorrect amino acids are incorporated or translation is interrupted prematurely. Deletions of several codons typically lead to a complete loss of the enzyme activity.

Instructions on generation of such mutations are prior art and can be found in known textbooks of genetics and molecular biology, such as e. g. the textbook by Knippers ("Molekulare Genetik" [Molecular Genetics], 6th edition, Georg Thieme Verlag, Stuttgart, Germany, 1995) *I.B.R.*, that by Winnacker ("Gene und Klone" [Genes and Clones], VCH Verlagsgesellschaft, Weinheim, Germany, 1990) *I.B.R.* or that by Hagemann ("Allgemeine Genetik" [General Genetics], Gustav Fischer Verlag, Stuttgart, 1986) *I.B.R.*

The invention also provides a vector containing one of the stated polynucleotides and coryneform bacteria acting as host cell which contain the vector or in which the cma gene is amplified.

The invention also provides
a polynucleotide which is capable of replication and comprises the nucleotide sequence SEQ ID No. 1, or consists of it,
a polynucleotide sequence which codes for a polypeptide which comprises the amino acid sequence SEQ ID No. 2, or consists of it,
a vector containing the DNA sequence of *C. glutamicum* which codes for the cma gene, contained in the vector (plasmid) pJC1cma, deposited in *Corynebacterium glutamicum* under number DSM 13248,
and coryneform bacteria serving as the host cell, which contain the vector or in which the cma gene is amplified.

The invention also provides polynucleotides which comprise the complete gene with the polynucleotide sequence corresponding to SEQ ID No. 1 or fragments thereof, and which are obtainable by screening by means of hybridization of a corresponding gene library with a probe which comprises the sequence of the polynucleotide mentioned, according to SEQ ID No. 1, or a fragment thereof, and isolation of the DNA sequence mentioned.

Polynucleotide sequences according to the invention are also suitable as hybridization probes for RNA, cDNA and DNA, in order to isolate, in the full length, cDNA which codes for cyclopropane-mycolic acid synthase and to isolate those cDNA or genes which have a high similarity of with the sequence of the cyclopropane-mycolic acid synthase gene.

Polynucleotide sequences according to the invention are furthermore suitable as primers for the polymerase chain reaction (PCR), for the preparation of DNA which codes for cyclopropane-mycolic acid synthases.

Such oligonucleotides which serve as probes or primers can comprise more than 30, preferably up to 30, particularly preferably up to 20, especially preferably at least 15 successive nucleotides. Oligonucleotides which have a length of at least 40 or 50 nucleotides are also suitable.

"Isolated" means separated out of its natural environment.

"Polynucleotide" in general relates to polyribonucleotides and polydeoxyribonucleotides, it being possible for these to be non-modified RNA or DNA or modified RNA or DNA.

"Polypeptides" is understood as meaning peptides or proteins which comprise two or more amino acids bonded via peptide bonds.

The polypeptides according to the invention include a polypeptide according to SEQ ID No. 2, in particular those with the biological activity of cyclopropane-mycolic acid synthase and also those which are homologous to the extent of at least 70% with the polypeptide according to SEQ ID No. 2, preferably to the extent of at least 80%, and particularly preferably those which are homologous to the extent of at least 90 to 95% with the polypeptide according to SEQ ID no. 2, and have the activity mentioned.

The invention moreover provides a method for the fermentative preparation of amino acids, in particular L-lysine and L-glutamate, using coryneform bacteria which in particular already produce an amino acid, and in which the nucleotide sequences which code for the cma gene are amplified, in particular over-expressed.

The cma gene of *C. glutamicum* which codes for cyclopropane-mycolic acid synthase is described for the first time in the present invention.

To isolate the cma gene or also other genes of *C. glutamicum*, a gene library of this microorganism was first set up in *E. coli*. The setting up of gene libraries is described in generally known textbooks and handbooks. The textbook by Winnacker: Gene und Klone, Eine Einführung in die Gentechnologie [Genes and Clones, An Introduction to Genetic Engineering] (Verlag Chemie, Weinheim, Germany, 1990) I.B.R. or the handbook by Sambrook et al.: Molecular Cloning, A Laboratory Manual (Cold Spring Harbor Laboratory Press, 1989) I.B.R. may be mentioned as an example. A well-known gene library is that of the *E. coli* K-12 strain W3110 set up in λ vectors by Kohara et al. (Cell 50, 495–508 (1987)) I.B.R. Bathe et al. (Molecular and General Genetics, 252:255–265, 1996) I.B.R. describe a gene library of *C. glutamicum* ATCC13032, which was set up with the aid of the cosmid vector SuperCos I (Wahl et al., 1987, Proceedings of the National Academy of Sciences USA, 84:2160–2164) I.B.R. in the *E. coli* K-12 strain NM554 (Raleigh et al., 1988, Nucleic Acids Research 16:1563–1575) I.B.R. Börmann et al. (Molecular Microbiology 6(3), 317–326)) (1992)) I.B.R. in turn describe a gene library of *C. glutamicum* ATCC13032 using the cosmid pHC79 (Hohn and Collins, Gene 11, 291–298 (1980)) I.B.R. To prepare a gene library of *C. glutamicum* in *E. coli* it is also possible to use plasmids such as pBR322 (Bolivar, Life Sciences, 25, 807–818 (1979)) I.B.R. or pUC9 (Vieira et al., 1982, Gene, 19:259–268) I.B.R. Suitable hosts are, in particular, those *E. coli* strains which are restriction- and recombination-defective. An example of these is the strain DH5αmcr, which has been described by Grant et al. (Proceedings of the National Academy of Sciences USA, 87 (1990) 4645–4649) I.B.R. The long DNA fragments cloned with the aid of cosmids can then in turn be subcloned and subsequently sequenced in the usual vectors which are suitable for sequencing, such as is described e.g. by Sanger et al. (Proceedings of the National Academy of Sciences of the United States of America, 74:5463–5467, 1977) I.B.R.

The new DNA sequence of *C. glutamicum* which codes for the cma gene and which, as SEQ ID No. 1, is a constituent of the present invention, was obtained in this manner. The amino acid sequence of the corresponding protein has moreover been derived from the present DNA sequence by the methods described above. The resulting amino acid sequence of the cma gene product is shown in SEQ ID No. 2.

Coding DNA sequences which result from SEQ ID No. 1 by the degeneracy of the genetic code are also a constituent of the invention. In the same way, DNA sequences which hybridize with SEQ ID No. 1 or parts of SEQ ID No. 1 are a constituent of the invention. Conservative amino acid exchanges, such as e.g. exchange of glycine for alanine or of aspartic acid for glutamic acid in proteins, are moreover known among experts as "sense mutations" which do not lead to a fundamental change in the activity of the protein, i.e. are of neutral function. It is moreover known that changes on the N and/or C terminus of a protein cannot substantially impair the function thereof or can even stabilize this. Information in this context can be found by the expert, inter alia, in Ben-Bassat et al. (Journal of Bacteriology 169:751–757 (1987)) I.B.R., in O'Regan et al. (Gene 77:237–251 (1989)) I.B.R., in Sahin-Toth et al. (Protein Sciences 3:240–247 (1994)) I.B.R., in Hochuli et al. (Bio/Technology 6:1321–1325 (1988)) I.B.R. and in known textbooks of genetics and molecular biology. Amino acid sequences which result in a corresponding manner from SEQ ID No. 2 are also a constituent of the invention.

In the same way, DNA sequences which hybridize with SEQ ID No. 1 or parts of SEQ ID No. 1 are a constituent of the invention. Finally, DNA sequences which are prepared by the polymerase chain reaction (PCR) using olognucleotide primers which result from SEQ ID NO. 1 are a constituent of the invention. Such oligonucleotides typically have a length of at least 15 nucleotides.

Instructions for identifying DNA sequences by means of hybridization can be found by the expert, inter alia, in the handbook "The DIG System Users Guide for Filter Hybridization" I.B.R. from Boehringer Mannheim GmbH (Mannheim, Germany, 1993) I.B.R. and in Liebl et al. (International Journal of Systematic Bacteriology (1991) 41: 255–260) I.B.R. Instructions for amplification of DNA sequences with the aid of the polymerase chain reaction (PCR) can be found by the expert, inter alia, in the handbook by Gait: Oligonukleotide synthesis: a practical approach (IRL Press, Oxford, UK, 1984) I.B.R. and in Newton and Graham: PCR (Spektrum Akademischer Verlag, Heidelberg, Germany, 1994) I.B.R.

In the work on the present invention, it has been found that coryneform bacteria produce amino acids, in particular L-lysine and L-glutamate, in an improved manner after amplification of the cma gene.

The genes or gene constructs under consideration can either be present in plasmids with a varying number of copies, or can be integrated and amplified in the chromosome. Alternatively, an over-expression of the genes in question can moreover be achieved by changing the composition of the media and the culture procedure.

Instructions in this context can be found by the expert, inter alia, in Martin et al. (Bio/Technology 5, 137–146 (1987)) I.B.R., in Guerrero et al. (Gene 138, 35–41 (1994)) I.B.R., Tsuchiya and Morinaga (Bio/Technology 6, 428–430

(1988)) I.B.R., in Eikmanns et al. (Gene 102, 93–98 (1991)) I.B.R., in European Patent Specification EPS 0 472 869 I.B.R., in U.S. Pat. No. 4,601,893 I.B.R., in Schwarzer and Pühler (Bio/Technology 9, 84–87 (1991) I.B.R., in Reinscheid et al. (Applied and Environmental Microbiology 60, 126–132 (1994)) I.B.R., in LaBarre et al. (Journal of Bacteriology 175, 1001–1007 (1993)) I.B.R., in patent application WO 96/15246, in Malumbres et al. (Gene 134, 15–24 (1993)) I.B.R., in Japanese Laid-Open Specification JP-A-10-229891, in Jensen and Hammer (Biotechnology and Bioengineering 58, 191–195 (1998)) I.B.R., in Makrides (Microbiological Reviews 60:512–538 (1996)) I.B.R. and in known textbooks of genetics and molecular biology.

By way of example, the cma gene according to the invention was over-expressed with the aid of plasmids.

Suitable plasmids are those which are replicated and expressed in coryneform bacteria. Numerous known plasmid vectors, such as e. g. pZ1 (Menkel et al., Applied and Environmental Microbiology (1989) 64: 549–554) I.B.R., pEKEx1 (Eikmanns et al., Gene 102:93–98 (1991)) or pHS2-1 (Sonnen et al., Gene 107:69–74 (1991)) I.B.R. are based on the cryptic plasmids pHM1519, pBL1 or pGA1. Other plasmid vectors, such as e. g. those based on pCG4 (U.S. Pat. No. 4,489,160) I.B.R., or pNG2 (Serwold-Davis et al., FEMS Microbiology Letters 66, 119–124 (1990)) I.B.R., or pAG1 (U.S. Pat. No. 5,158,891) I.B.R., can be used in the same manner.

An example of a plasmid, with the aid of which the cma gene can be over-expressed is pJC1cma (FIG. 1), which is based on the *E. coli—C. glutamicum* shuttle vector pJC1 (Cremer et al., 1990, Molecular and General Genetics 220: 478–480) I.B.R. and contains the DNA sequence of *Corynebacterium glutamicum* which codes for the cma gene. It is contained in the strains ATCC 13032/pJC1cma and DSM5715/pJC1cma.

Plasmid vectors which are moreover suitable are those with the aid of which the method of gene amplification by integration into the chromosome can be used, as has been described, for example, by Reinscheid et al. (Applied and Environmental Microbiology 60, 126–132 (1994)) I.B.R. for duplication or amplification of the hom-thrB operon. In this method, the complete gene is cloned in a plasmid vector which can replicate in a host (typically *E. coli*), but not in *C. glutamicum*. Possible vectors are, for example, pSUP301 (Simon et al., Bio/Technology 1, 784–791 (1983)) I.B.R., pK18mob or pK19mob (Schäfer et al., Gene 145, 69–73 (1994)) I.B.R., pGEM-T (Promega corporation, Madison, Wis., USA), pCR2.1-TOPO (Shuman (1994) I.B.R. Journal of Biological Chemistry 269:32678–84; U.S. Pat. No. 5,487, 993) I.B.R., pCR®Blunt (Invitrogen, Groningen, Holland; Bernard et al., Journal of Molecular Biology, 234: 534–541 (1993)) I.B.R. or pEM1 (Schrumpf et al, 1991, Journal of Bacteriology 173:4510–4516) I.B.R. The plasmid vector which contains the gene to be amplified is then transferred into the desired strain of *C. glutamicum* by conjugation or transformation. The method of conjugation is described, for example, by Schäfer et al. (Applied and Environmental Microbiology 60, 756–759 (1994)) I.B.R. Methods for transformation are described, for example, by Thierbach et al. (Applied Microbiology and Biotechnology 29, 356–362 (1988)) I.B.R., Dunican and Shivnan (Bio/Technology 7, 1067–1070 (1989)) I.B.R. and Tauch et al. (FEMS Microbiological Letters 123, 343–347 (1994)) I.B.R. After homologous recombination by means of a "cross over" event, the resulting strain contains at least two copies of the gene in question.

In addition, it may be advantageous for the production of amino acids, in particular L-lysine and L-glutamate, to amplify or over-express one or more enzymes of the particular biosynthesis pathway, of glycolysis, of anaplerosis, of the citric acid cycle or of amino acid export, in addition to the cma gene.

Thus, for example, for the preparation of L-lysine, one or more genes chosen from the group consisting of the dapA gene which codes for dihydrodipicolinate synthase (EP-B 0 197 335 I.B.R.), or the dapE gene which codes for succinyl diaminopimelate desuccinylase, or the lysC gene which codes for a feed-back resistant aspartate kinase (Kalinowski et al. (1990), Molecular and General Genetics 224, 317–324 I.B.R.), or the gap gene which codes for glyceraldehyde 3-phosphate dehydrogenase (Eikmanns (1992), Journal of Bacteriology 174:6076–6086 I.B.R.), or the tpi gene which codes for triose phosphate isomerase (Eikmanns (1992), Journal of Bacteriology 174:6076–6086 I.B.R.), or the pgk gene which codes for 3-phosphoglycerate kinase (Eikmanns (1992), Journal of Bacteriology 174:6076–6086 I.B.R.), or the pyc gene which codes for pyruvate carboxylase (DE-A-19831609 I.B.R.), or the mqo gene which codes for malate-quinone oxidoreductase (Molenaar et al., European Journal of Biochemistry 254, 395–403 (1998) I.B.R.), or the lysE gene which codes for lysine export (DE-A-195 48 222 I.B.R.)

can be amplified, in particular over-expressed or amplified, at the same time.

Furthermore, for example, for the preparation of L-glutamate, one or more genes chosen from the group consisting of the gdh gene which codes for glutamate dehydrogenase (DE: 19907347.3 I.B.R.) and/or the pyc gene which codes for pyruvate carboxylase (Peters-Wendisch et al. (1998), Microbiology 144: 915–927 I.B.R.)

can be amplified, in particular over-expressed or amplified, at the same time.

In addition to amplification of the cma gene it may moreover be advantageous for the production of L-lysine to attenuate the pck gene which codes for phosphoenol pyruvate carboxykinase (DE 199 50 409.1, DSM 13047 I.B.R.) and/or the pgi gene which codes for glucose 6-phosphate isomerase (U.S. Ser. No. 09/396,478, DSM 12969 I.B.R.)

at the same time.

In addition to amplification of the cma gene it may moreover be advantageous for the production of L-glutamate to attenuate the odhA gene which codes for α-ketoglutarate dehydrogenase (WO 9534672 A1 951221* I.B.R.), or the dtsR1 gene which codes for the DtsR1 protein (WO 952324 A1 950831* I.B.R.), or the dtsR2 gene which codes for the DtsR2 protein (WO 9902692A A1 990121* I.B.R.)

at the same time.

In addition to over-expression of the cma gene it may moreover be advantageous for the production of amino acids, in particular L-lysine and L-glutamate, to eliminate undesirable side reactions (Nakayama: "Breeding of Amino Acid Producing Micro-organisms", in: Overproduction of Microbial Products, Krumphanzl, Sikyta, Vanek (eds.), Academic Press, London, UK, 1982 I.B.R.).

The microorganisms prepared according to the invention can be cultured continuously or discontinuously in the batch method (batch culture) or in the fed batch (feed method) or repeated fed batch method (repetitive feed method) for the purpose of production of amino acids, in particular L-lysine. A summary of known culture methods are described in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991) I.B.R.) or in the textbook by Storhas (Bioreaktoren und periphere Einrichtungen [Bioreactors and Peripheral Equipment] (Vieweg Verlag, Braunschweig/Wiesbaden, 1994) I.B.R.).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981 I.B.R.). Sugars and carbohydrates, such as e. g. glucose, sucrose, lactose, fructose, maltose, molasses, starch and cellulose, oils and fats, such as e. g. soya oil, sunflower oil, groundnut oil and coconut fat, fatty acids, such as e. g. palmitic acid, stearic acid and linoleic acid, alcohols, such as e.g. glycerol and ethanol, and organic acids, such as e.g. acetic acid, can be used as the source of carbon. These substances can be used individually or as a mixture. Organic nitrogen-containing compounds, such as peptones, yeast extract, meat extract, malt extract, corn steep liquor, soy bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture. Phosphoric acid, potassium dihydrogen phosphate or dipotassium hydrogen phosphate or the corresponding sodium-containing salts can be used as the source of phosphorus. The culture medium must moreover comprise salts of metals, such as e.g. magnesium sulfate or iron sulfate, which are necessary for growth. Finally, essential growth substances, such as amino acids and vitamins, can be employed in addition to the abovementioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as e.g. fatty acid polyglycol esters, can be employed to control the development of foam. Suitable substances having a selective action, such as e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 20° C. to 45° C., and preferably 25° C. to 40° C. Culturing is continued until a maximum of lysine has formed. This target is usually reached within 10 hours to 160 hours.

The analysis of L-lysine or L-glutamate can be carried out by anion exchange chromatography with subsequent ninhydrin derivatization, as described by Spackman et al. (Analytical Chemistry, 30, (1958), 1190) I.B.R.

The following microorganism has been deposited at the Deutsche Sammlung für Mikrorganismen und Zellkulturen (DSMZ=German Collection of Microorganisms and Cell Cultures, Braunschweig, Germany) in accordance with the Budapest Treaty:

Corynebacterium glutamicum strain DSM5715/pJC1cma as DSM 13248

The method according to the invention is used for the fermentative preparation of amino acids, in particular L-lysine and L-glutamate.

Legend to the figure:

FIG. 1: Map of the plasmid pJC1cma

The abbreviations and designations used have the following meaning:

| | |
|---|---|
| ORF2, rep: | Plasmid-coded replication origin C. glutamicum (of pHM1519) |
| cma: | cma (cyclopropane-mycolic acid synthase) gene from C. glutamicum ATCC13032 |
| Kan: | Kanamycin resistance gene |
| BamHI: | Cleavage site of the restriction enzyme BamHI |
| XbaI: | Cleavage site of the restriction enzyme XbaI |
| SalI: | Cleavage site of the restriction enzyme SalI |
| PstI: | Cleavage site of the restriction enzyme PstI |
| XmaI: | Cleavage site of the restriction enzyme XmaI |
| BglII: | Cleavage site of the restriction enzyme EglII |
| SphI: | Cleavage site of the restriction enzyme SphI |
| EcoRI: | Cleavage site of the restriction enzyme EcoRI |

EXAMPLES

The present invention is explained in more detail in the following with the aid of embodiment examples.

Example 1

Preparation of a Genomic Cosmid Gene Library From Corynebacterium glutamicum ATCC 13032

Chromosomal DNA from Corynebacterium glutamicum ATCC 13032 was isolated as described by Tauch et al. (1995, Plasmid 33:168–179) I.B.R. and partly cleaved with the restriction enzyme Sau3AI (Amersham Pharmacia, Freiburg, Germany, Product Description Sau3AI, Code no. 27-0913-02) I.B.R. The DNA fragments were dephosphorylated with shrimp alkaline phosphatase (Roche Molecular Biochemicals, Mannheim, Germany, Product Description SAP, Code no. 1758250) I.B.R. The DNA of the cosmid vector SuperCos1 (Wahl et al. (1987) Proceedings of the National Academy of Sciences USA 84:2160–2164 I.B.R.), obtained from Stratagene (La Jolla, USA, Product Description SuperCos1 Cosmid Vektor Kit, Code no. 251301), was cleaved with the restriction enzyme XbaI (Amersham Pharmacia, Freiburg, Germany, Product Description XbaI, Code no. 27-0948-02) and likewise dephosphorylated with shrimp alkaline phosphatase. The cosmid DNA was then cleaved with the restriction enzyme BamHI (Amersham Pharmacia, Freiburg, Germany, Product Description BamHI, Code no. 27-0868-04). The cosmid DNA treated in this manner was mixed with the treated ATCC 13032 DNA and the batch was treated with T4 DNA ligase (Amersham Pharmacia, Freiburg, Germany, Product Description T4-DNA-Ligase, Code no. 27-0870-04). The ligation mixture was then packed in phages with the aid of Gigapack II XL Packing Extracts (Stratagene, La Jolla, USA, Product Description Gigapack II XL Packing Extract, Code no. 200217). For infection of the E. coli strain NM554 (Raleigh et al. 1988, Nucleic Acid Research 16:1563–1575 I.B.R.) the cells were taken up in 10 mM $MgSO_4$ and mixed with an aliquot of the phage suspension. The infection and titering of the cosmid library were carried out as described by Sambrook et al. (1989, Molecular Cloning: A laboratory Manual, Cold Spring Harbor I.B.R.), the cells being plated out on LB agar (Lennox, 1955, Virology, 1:190 I.B.R.) with 100 mg/l ampicillin. After incubation overnight at 37° C., recombinant individual clones were selected.

Example 2

Isolation and Sequencing of the cma Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Molecular Biochemicals, Mannheim, Germany, Product Description SAP, Product No. 1758250). After separation by gel electrophoresis, the cosmid fragments in the size range of 1500 to 2000 bp were isolated with the QiaExII Gel Extraction Kit (Product No. 20021, Qiagen, Hilden, Germany). The DNA of the sequencing vector pZero-1, obtained from Invitrogen (Groningen, Holland, Product Description Zero Background Cloning Kit, Product No. K2500-01) was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A laboratory Manual, Cold Spring Harbor) I.B.R., the DNA mixture being incubated overnight with T4 ligase (Pharmacia Biotech, Freiburg, Germany). This ligation mixture was then transformed by means of electroporation (Tauch et al. 1994, FEMS Microbiol Letters, 123:343–7 I.B.R.) into the *E. coli* strain DH5αMCR (Grant, 1990, Proceedings of the National Academy of Sciences U.S.A., 87:4645–4649 I.B.R.) and plated out on LB agar (Lennox, 1955, Virology, 1:190 I.B.R.) with 50 mg/l zeocin. The plasmid preparation of the recombinant clones was carried out with Biorobot 9600 (Product No. 900200, Qiagen, Hilden, Germany). The sequencing was carried out by the dideoxy chain-stopping method of Sanger et al. (1977, Proceedings of the National Academy of Sciences U.S.A., 74:5463–5467) I.B.R. with modifications according to Zimmermann et al. (1990, Nucleic Acids Research, 18:1067) I.B.R. The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217–231 I.B.R.) version 97-0. The individual sequences of the PZero1 derivatives were assembled to a continuous contig. The computer-assisted coding region analysis was prepared with the XNIP program (Staden, 1986, Nucleic Acids Research, 14:217–231 I.B.R.). Further analyses were carried out with the "BLAST search program" (Altschul et al., 1997, Nucleic Acids Research, 25:3389–3402 I.B.R.), against the non-redundant databank of the "National Center for Biotechnology Information" (NCBI, Bethesda, Md., USA I.B.R.).

The resulting nucleotide sequence is shown in SEQ ID No. 1. Analysis of the nucleotide sequence showed an open reading frame of 1353 base pairs, which was called the cma gene. The cma gene codes for a protein of 451 amino acids.

The following microorganism has been deposited at the Deutsche Sammlung füar Mikrorganismen und Zellkulturen (DSMZ=German Collection of Microorganisms and Cell Cultures, Braunschweig, Germany) in accordance with the Budapest Treaty:

*Corynebacterium glutamicum* strain DSM5715/pJC1cma as DSM 13248

Example 3

Cloning of the cma gene in the vector pJC1

Chromosomal DNA from *Corynebacterium glutamicum* ATCC 13032 was isolated as described in Tauch et al., (1995, Plasmid 33:168–179) I.B.R. A DNA fragment which carries the ema gene was amplified with the aid of the polymerase chain reaction. The following primers were used for this:

```
SEQ ID NO:3  5'-TGC TCT AGA AAA GCA GGT GGG AAA TGG GAC AGT-3'

SEQ ID NO:3  5'-TGC TCT AGA TGG CAG AGC TAG GCG GAC ATA AAT-3'
```

The two oligonucleotides carry the sequence for the cleavage site of the restriction enzyme XbaI (nucleotides underlined). The primers shown were synthesized by MWG Biotech (Ebersberg, Germany) and the PCR reaction was carried out with them by the standard PCR method of Innis et al., (PCR protocol. A guide to methods and applications, 1990, Academic Press) I.B.R. The primers allow amplification of a DNA fragment of 1653 bp in size, which carries the cma gene from *Corynebacterium glutamicum*.

After separation by gel electrophoresis, the PCR fragment was isolated from the agarose gel with the QiaExII Gel Extraction Kit (Product No. 20021, Qiagen, Hilden, Germany).

The PCR fragment obtained in this manner was cleaved completely with the restriction enzyme XbaI. The cma fragment approx. 1659 bp in size was isolated from the agarose gel with the QiaExII Gel Extraction Kit (Product No. 20021, Qiagen, Hilden, Germany).

The *E. coli—C. glutamicum* shuttle vector pJC1 (Cremer et al., 1990, Molecular and General Genetics 220: 478–480) I.B.R. was used as the vector. This plasmid was also cleaved completely with the restriction enzyme XbaI and then dephosphorylated with shrimp alkaline phosphatase (Roche Diagnostics GmbH, Mannheim, Germany, Product Description SAP, Product No. 1758250).

The cma fragment obtained in this manner was mixed with the prepared vector pJC1 and the batch was treated with T4 DNA ligase (Amersham Pharmacia, Freiburg, Germany, Product Description T4-DNA-Ligase, Code no. 27-0870-04). The ligation batch was transformed in the *E. coli* strain DH5α (Hanahan, In: DNA cloning. A practical approach. Vol. I. IRL-Press, Oxford, Washington, D.C., USA I.B.R.). Selection of plasmid-carrying cells was made by plating out the transformation batch on LB agar (Lennox, 1955, Virology, 1:190 I.B.R.) with 50 mg/l kanamycin. After incubation overnight at 37° C., recombinant individual clones were selected. Plasmid DNA was isolated from a transformant with the Qiaprep Spin Miniprep Kit (Product No. 27106, Qiagen, Hilden, Germany) in accordance with the manufacturer's instructions and cleaved with the restriction enzyme XbaI to check the plasmid by subsequent agarose gel electrophoresis. The resulting plasmid was called pJC1cma.

Example 4

Transformation of the strains DSM5715 and ATCC13032 with the plasmid pJC1cma

The strains DSM5715 and ATCC13032 were transformed with the plasmid pJC1cma using the electroporation method described by Liebl et al., (FEMS Microbiology Letters, 53:299–303 (1989)) I.B.R. Selection of the transformants took place on LBHIS agar comprising 18.5 g/l brain-heart infusion broth, 0.5M sorbitol, 5 g/l Bacto-tryptone, 2.5 g/l Bacto-yeast extract, 5 g/l NaCl and 18 g/l Bacto-agar, which had been supplemented with 25 mg/l kanamycin. Incubation was carried out for 2 days at 33° C.

Plasmid DNA was isolated from in each case one transformant by conventional methods (Peters-Wendisch et al., 1998, Microbiology 144, 915–927 I.B.R.) and cleaved with the restriction endonuclease BamHI, to check the plasmid by subsequent agarose gel electrophoresis. The resulting strains were called DSM5715/pJC1cma and ATCC13032/pJC1cma.

The following microorganism has been deposited at the Deutsche Sammlung für Mikrorganismen und Zellkulturen (DSMZ=German Collection of Microorganisms and Cell Cultures, Braunschweig, Germany) in accordance with the Budapest Treaty:

*Corynebacterium glutamicum* strain DSM 5715/pJC1cma as DSM 13248

Example 5

Preparation of L-glutamate with the strain TCC13032/pJC1cma

The *C. glutamicum* strain ATCC13032/pJC1cma obtained in example 4 was cultured in a nutrient medium suitable for the production of glutamate and the glutamate content in the culture supernatant was determined.

For this, the strain was first incubated on an agar plate with the corresponding antibiotic (brain-heart agar with kanamycin (50 mg/l)) for 24 hours at 33° C. Starting from this agar plate culture, a preculture was seeded (10 ml medium in a 100 ml conical flask). The complete medium CgIII (2.5 g/l NaCl, 10 g/l Bacto-peptone, 10 g/l Bacto-yeast extract, pH 7.4, 20 g/l Glucose (autoclaved separately) was used as the medium for the preculture. Kanamycin (25 mg/l) was added to this. The preculture was incubated for 16 hours at 33° C. at 240 rpm on a shaking machine. A main culture was seeded from this preculture such that the initial OD (660 nm) of the main culture was 0.1. Medium CgXII was used for the main culture.

After preculturing in medium CgIII (Keilhauer et al. 1993, Journal of Bacteriology 175:5595–5603 I.B.R.), the strain ATCC13032/pJC1cma was cultured in the production medium CgXII (Keilhauer et al. 1993, Journal of Bacteriology 175:5595–5603 I.B.R.)I. 4% glucose and 50 mg/l kanamycin sulfate were added.

For induction of the glutamate formation, 20 g Tween 60 (P-1629, Sigma-Aldrich, Deisenhofen, Germany) plus 80 ml water were mixed and autoclaved. About 4 hours after the inoculation, 75 µl of this Tween solution were added to the culture and culturing was continued.

Culturing is carried out in a 10 ml volume in a 100 ml conical flask with baffles. Kanamycin (25 mg/l) was added. Culturing was carried out at 33° C. and 80% atmospheric humidity.

After 48 hours, the OD was determined at a measurement wavelength of 660 nm with a Biomek 1000 (Beckmann Instruments GmbH, Munich). The amount of glutamate formed was determined with an amino acid analyzer from Eppendorf-BioTronik (Hamburg, Germany) by ion exchange chromatography and post-column derivatization with ninhydrin detection.

The result of the experiment is shown in table 1.

TABLE 1

| Strain | OD (660) | Glutamate HCl mM |
|---|---|---|
| ATCC13032/pJC1cma | 14.7 | 106 |
| ATCC13032 | 13.8 | 94 |

Example 6

Preparation of Lysine

The *C. glutamicum* strain DSM5715/pJC1cma obtained in example 4 was cultured in a nutrient medium suitable for the production of lysine and the lysine content in the culture supernatant was determined.

For this, the strain was first incubated on an agar plate with the corresponding antibiotic (brain-heart agar with kanamycin (50 mg/l)) for 24 hours at 33° C. Starting from this agar plate culture, a preculture was seeded (10 ml medium in a 100 ml conical flask). The complete medium CgIII (2.5 g/l NaCl, 10 g/l Bacto-peptone, 10 g/l Bacto-yeast extract, pH7.4, 20 g/l Glucose (autoclaved separately) was used as the medium for the preculture. Kanamycin (25 mg/l) was added to this. The preculture was incubated for 16 hours at 33° C. at 240 rpm on a shaking machine. A main culture was seeded from this preculture such that the initial OD (660 nm) of the main culture was 0.1. Medium MM was used for the main culture.

Medium MM

| | |
|---|---|
| CSL (corn steep liquor) | 5 g/l |
| MOPS (morpholinopropanesulfonic acid) | 20 g/l |
| Glucose (autoclaved separately) | 50 g/l |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |
| L-Leucine | 0.1 g/l |
| $CaCO_3$ | 25 g/l |

The CSL, MOPS and the salt solution were brought to pH 7 with aqueous ammonia and autoclaved. The sterile substrate and vitamin solutions were then added, as well as the $CaCO_3$ autoclaved in the dry state.

Culturing is carried out in a 10 ml volume in a 100 ml conical flask with baffles. Kanamycin (25 µg/l) was added. Culturing was carried out at 33° C. and 80% atmospheric humidity.

After 24 hours, the OD was determined at a measurement wavelength of 660 nm with a Biomek 1000 (Beckmann Instruments GmbH, Munich). The amount of lysine formed was determined with an amino acid analyzer from Eppendorf-BioTronik (Hamburg, Germany) by ion exchange chromatography and post-column derivatization with ninhydrin detection.

The result of the experiment is shown in table 1.

TABLE 2

| Strain | OD (660) | Lysine HCl g/l |
|---|---|---|
| DSM5715/pJC1cma | 12.47 | 8.51 |
| DSM5715 | 11.90 | 7.80 |

What is claimed is:

1. An isolated polynucleotide which encodes a protein comprising the amino acid sequence of SEQ ID NO: 2, wherein said protein has cyclopropane-mycolic acid synthase activity.

2. The isolated polynucleotide according to claim 1, wherein said polynucleotide is isolated from a coryneform bacterium.

3. An isolated polynucleotide comprising nucleotides 248 to 1600 of SEQ ID NO: 1 which encodes a cyclopropane-mycolic acid synthase.

4. An isolated polynucleotide comprising SEQ ID NO: 1.

5. An isolated polynucleotide consisting of SEQ ID NO: 1 or fragment thereof which encodes a protein consisting of the amino acid sequence of SEQ ID NO: 2.

6. An isolated polynucleotide comprising the complement of SEQ ID NO: 1.

7. An isolated polynucleotide comprising a nucleotide sequence that is at least 70% identical to the polynucleotide of SEQ ID NO: 1, wherein said polynucleotide encodes a protein comprising the amino acid sequence of SEQ ID NO: 2, and wherein said protein has cyclopropane-mycolic acid synthase activity.

8. The isolated polynucleotide according to claim 1, wherein said nucleotide sequence is at least 80% identical to the polynucleotide of SEQ ID NO: 1.

9. The isolated polynucleotide according to claim 7, wherein said nucleotide sequence is at least 90% identical to the polynucleotide of SEQ ID NO: 1.

10. The isolated polynucleotide according to claim 7, wherein said polynucleotide is isolated from a Coryneform bacterium.

11. An isolated polynucleotide consisting of at least 15 consecutive nucleotides selected from one of SEQ ID NO: 1 or a complement of SEQ ID NO: 1.

12. The isolated polynucleotide of claim 11, wherein the polynucleotide is a probe that detects a polynucleotide that encodes a cma polypeptide consisting of SEQ ID NO: 2.

13. The isolated polynucleotide of claim 11, wherein the polynucleotide is a primer for use in a polymerase chain reaction for synthesizing a polynucleotide encoding a cma polypeptide consisting of SEQ ID NO: 2.

14. A vector comprising the isolated polynucleotide sequence of any one of claims 11 to 10.

15. A bacterium comprising the vector of claim 14.

16. A pJC1cma vector deposited under DSM13248.

17. A transformed bacterium comprising an isolated polynueleotide which encodes a protein comprising the amino acid sequence of SEQ ID NO: 2, wherein said protein has cyclopropane-mycolic acid synthase activity.

18. The transformed bacterium of claim 17, wherein said polynucleotide is in several copies.

19. The transformed bacterium of claim 18, wherein said polynucleotide is overexpressed.

20. The transformed bacterium of claim 17, wherein the bacterium used for transformation is selected from the group consisting of *Corynebacterium glutamicum* (ATCC 13032), *Corynebacterium acetoglutamicum* (ATCC 15806), *Corynebacterium acetoacidophilum* (ATCC 13870), *Corynebacterium thermoaminogenes* (FERM BP-1539), *Corynebacterium melassecola* (ATCC 17965), *Brevibacterium flavum* (ATCC 14067), *Brevibacterium lactofermentum* (ATCC13869) and *Brevibacterium divaricatum* (ATCC 14020).

21. A *Corynebacterium glutamicum* DSM5715/pJC1cma deposited under DSM 13248.

* * * * *

SEQUENCE LISTING

<160> NUMBER OF SEQ ID NOS: 4

<210> SEQ ID NO 1
<211> LENGTH: 1801
<212> TYPE: DNA
<213> ORGANISM: Corynebacterium glutamicum
<220> FEATURE:
<221> NAME/KEY: CDS
<222> LOCATION: (248)..(1600)
<223> OTHER INFORMATION:

<400> SEQUENCE: 1

```
ctccgatgca ccagagggag catttaacag agaaatcgaa cgcgtcatgg cagagctagg     60
cggacataaa tcgctgtact ccgaagcgtt ctacaccagg gaagactttg aaaaacttta    120
tggcggaacc atcccggcgc tgctaaaaaa gcagtgggat ccccacagcc gattccccgg    180
tttgtatgaa aagacagtaa aaggcgccta ggatcgctca ctgtaggtag aggcttgtgg    240 tcactac ttg tgg cca cat ttt aaa aaa atg cac aag aag aga aag caa       289
        Leu Trp Pro His Phe Lys Lys Met His Lys Lys Arg Lys Gln
         1               5                  10 agc att atg agt aac gcc gta gcg cag gac ctc atg acc atc gcc gac       337
Ser Ile Met Ser Asn Ala Val Ala Gln Asp Leu Met Thr Ile Ala Asp
 15              20                  25                  30 atc gtc gag gcc acg acc act gca ccc atc cca ttc cac atc act gcc       385
Ile Val Glu Ala Thr Thr Thr Ala Pro Ile Pro Phe His Ile Thr Ala
                 35                  40                  45 ttc gat gga agc ttc act ggc cct gaa gat gct ccc tac cag ctg ttt       433
Phe Asp Gly Ser Phe Thr Gly Pro Glu Asp Ala Pro Tyr Gln Leu Phe
             50                  55                  60 gtt gcc aac acg gat gca gta tcc tac atc gca aca gcg cca gga gat       481
Val Ala Asn Thr Asp Ala Val Ser Tyr Ile Ala Thr Ala Pro Gly Asp
         65                  70                  75 ttg ggt ttg gca cgt gcc tac ctc atg gga gac ctc atc gtg gaa ggt       529
Leu Gly Leu Ala Arg Ala Tyr Leu Met Gly Asp Leu Ile Val Glu Gly
     80                  85                  90 gag cat ccc ggc cat cct tat ggg atc ttt gat gcg ttg aag gag ttc       577
Glu His Pro Gly His Pro Tyr Gly Ile Phe Asp Ala Leu Lys Glu Phe
 95                 100                 105                 110 tac cgc tgc ttc aaa cgc cca gat gca tcc acc acc ttg cag atc atg       625
Tyr Arg Cys Phe Lys Arg Pro Asp Ala Ser Thr Thr Leu Gln Ile Met
                115                 120                 125 tgg act ctg cgg aaa atg aat gcc tta aaa ttc cag gaa att cca cca       673
Trp Thr Leu Arg Lys Met Asn Ala Leu Lys Phe Gln Glu Ile Pro Pro
            130                 135                 140 atg gaa caa gcc cct gca tgg cgt aaa gca ctg atc aac ggg cta gca       721
Met Glu Gln Ala Pro Ala Trp Arg Lys Ala Leu Ile Asn Gly Leu Ala
        145                 150                 155
```

-continued

| | | |
|---|---|---|
| tcc agg cac tcg aaa tcc cgc gac aag aaa gcc att agc tac cac tac<br>Ser Arg His Ser Lys Ser Arg Asp Lys Lys Ala Ile Ser Tyr His Tyr<br>160                          165                       170 | 769 |
| gac gtg ggc aat gag ttc tac tcc ctg ttt tta gat gat tcc atg acc<br>Asp Val Gly Asn Glu Phe Tyr Ser Leu Phe Leu Asp Asp Ser Met Thr<br>175                       180                     185                 190 | 817 |
| tat acc tgc gcg tat tat cca acg cca gaa tca agt ttg gaa gaa gcc<br>Tyr Thr Cys Ala Tyr Tyr Pro Thr Pro Glu Ser Ser Leu Glu Glu Ala<br>                  195                     200                     205 | 865 |
| caa gaa aac aaa tac cgc ctc atc ttt gaa aaa ctg cgt ctg aaa gaa<br>Gln Glu Asn Lys Tyr Arg Leu Ile Phe Glu Lys Leu Arg Leu Lys Glu<br>         210                     215                     220 | 913 |
| ggc gat cgc ctc cta gac gtg gga tgc ggt tgg gga ggc atg gtc cgc<br>Gly Asp Arg Leu Leu Asp Val Gly Cys Gly Trp Gly Gly Met Val Arg<br>225                          230                       235 | 961 |
| tac gcc gcc aaa cac ggt gtg aaa gcc atc gga gtt acg ctg tct gaa<br>Tyr Ala Ala Lys His Gly Val Lys Ala Ile Gly Val Thr Leu Ser Glu<br>         240                     245                     250 | 1009 |
| cag caa tat gag tgg ggt caa gca gag atc aaa cgc caa ggt ttg gaa<br>Gln Gln Tyr Glu Trp Gly Gln Ala Glu Ile Lys Arg Gln Gly Leu Glu<br>255                          260                     265                 270 | 1057 |
| gac ctc gcg gaa att cgc ttc atg gat tac cgc gat gtt cca gaa act<br>Asp Leu Ala Glu Ile Arg Phe Met Asp Tyr Arg Asp Val Pro Glu Thr<br>                  275                     280                     285 | 1105 |
| gga ttc gat gcg atc tca gca atc ggc atc att gaa cac atc ggt gtg<br>Gly Phe Asp Ala Ile Ser Ala Ile Gly Ile Ile Glu His Ile Gly Val<br>         290                     295                     300 | 1153 |
| aac aac tat ccc gac tac ttt gaa ttg ctc agc agc aaa ctc aaa aca<br>Asn Asn Tyr Pro Asp Tyr Phe Glu Leu Leu Ser Ser Lys Leu Lys Thr<br>305                          310                     315 | 1201 |
| ggc gga ctg atg ctc aac cac agc atc acc tac cca gac aac cgc ccc<br>Gly Gly Leu Met Leu Asn His Ser Ile Thr Tyr Pro Asp Asn Arg Pro<br>320                          325                     330 | 1249 |
| cgc cac gca ggt gca ttt att gat cgc tac att ttc ccc gac ggt gaa<br>Arg His Ala Gly Ala Phe Ile Asp Arg Tyr Ile Phe Pro Asp Gly Glu<br>335                          340                     345                 350 | 1297 |
| ctc act ggc tct ggc acc ctg atc aag cac atg cag gac aac ggt ttc<br>Leu Thr Gly Ser Gly Thr Leu Ile Lys His Met Gln Asp Asn Gly Phe<br>                  355                     360                     365 | 1345 |
| gaa gtg ctg cac gaa gaa aac ctc cgc ttt gat tac caa cgc acc ctg<br>Glu Val Leu His Glu Glu Asn Leu Arg Phe Asp Tyr Gln Arg Thr Leu<br>         370                     375                     380 | 1393 |
| cac gcg tgg tgc gaa aac ctc aaa gaa aat tgg gag gaa gca gtt gaa<br>His Ala Trp Cys Glu Asn Leu Lys Glu Asn Trp Glu Glu Ala Val Glu<br>385                          390                     395 | 1441 |
| ctc gcc ggt gaa ccc act gca cga ctc ttt ggc ctg tac atg gca ggt<br>Leu Ala Gly Glu Pro Thr Ala Arg Leu Phe Gly Leu Tyr Met Ala Gly<br>400                          405                     410 | 1489 |
| tcg gaa tgg gga ttt gcc cac aac atc gtc cag ctg cac caa gta ctg<br>Ser Glu Trp Gly Phe Ala His Asn Ile Val Gln Leu His Gln Val Leu<br>415                          420                     425                 430 | 1537 |
| ggt gtg aaa ctc gat gag cag gga agt cgc gga gaa gtt cct gaa aga<br>Gly Val Lys Leu Asp Glu Gln Gly Ser Arg Gly Glu Val Pro Glu Arg<br>                  435                     440                     445 | 1585 |
| atg tgg tgg act atc taaagaaaca atgtttcttt ttaaggttcc ctaggggcag<br>Met Trp Trp Thr Ile<br>                  450 | 1640 |
| gagttaattg taggtaaact cgactagcaa ttagcgactg tcccatttcc cacctgcttt | 1700 |

```
tgcggatttc aacactttca ggatgcatct gtaactatgc ccatgccaca ccccatgttt   1760
atcgatgtct ccttcccacc cgcggagacc tgtagttaac c                       1801
```

<210> SEQ ID NO 2
<211> LENGTH: 451
<212> TYPE: PRT
<213> ORGANISM: Corynebacterium glutamicum

<400> SEQUENCE: 2

```
Leu Trp Pro His Phe Lys Lys Met His Lys Arg Lys Gln Ser Ile
1               5                   10                  15

Met Ser Asn Ala Val Ala Gln Asp Leu Met Thr Ile Ala Asp Ile Val
                20                  25                  30

Glu Ala Thr Thr Thr Ala Pro Ile Pro Phe His Ile Thr Ala Phe Asp
                35                  40                  45

Gly Ser Phe Thr Gly Pro Glu Asp Ala Pro Tyr Gln Leu Phe Val Ala
            50                  55                  60

Asn Thr Asp Ala Val Ser Tyr Ile Ala Thr Ala Pro Gly Asp Leu Gly
65                  70                  75                  80

Leu Ala Arg Ala Tyr Leu Met Gly Asp Leu Ile Val Glu Gly Glu His
                85                  90                  95

Pro Gly His Pro Tyr Gly Ile Phe Asp Ala Leu Lys Glu Phe Tyr Arg
            100                 105                 110

Cys Phe Lys Arg Pro Asp Ala Ser Thr Thr Leu Gln Ile Met Trp Thr
        115                 120                 125

Leu Arg Lys Met Asn Ala Leu Lys Phe Gln Glu Ile Pro Pro Met Glu
    130                 135                 140

Gln Ala Pro Ala Trp Arg Lys Ala Leu Ile Asn Gly Leu Ala Ser Arg
145                 150                 155                 160

His Ser Lys Ser Arg Asp Lys Lys Ala Ile Ser Tyr His Tyr Asp Val
                165                 170                 175

Gly Asn Glu Phe Tyr Ser Leu Phe Leu Asp Asp Ser Met Thr Tyr Thr
            180                 185                 190

Cys Ala Tyr Tyr Pro Thr Pro Glu Ser Ser Leu Glu Glu Ala Gln Glu
        195                 200                 205

Asn Lys Tyr Arg Leu Ile Phe Glu Lys Leu Arg Leu Lys Glu Gly Asp
    210                 215                 220

Arg Leu Leu Asp Val Gly Cys Gly Trp Gly Gly Met Val Arg Tyr Ala
225                 230                 235                 240

Ala Lys His Gly Val Lys Ala Ile Gly Val Thr Leu Ser Glu Gln Gln
                245                 250                 255

Tyr Glu Trp Gly Gln Ala Glu Ile Lys Arg Gln Gly Leu Glu Asp Leu
            260                 265                 270

Ala Glu Ile Arg Phe Met Asp Tyr Arg Asp Val Pro Glu Thr Gly Phe
        275                 280                 285

Asp Ala Ile Ser Ala Ile Gly Ile Ile Glu His Ile Gly Val Asn Asn
    290                 295                 300

Tyr Pro Asp Tyr Phe Glu Leu Leu Ser Ser Lys Leu Lys Thr Gly Gly
305                 310                 315                 320

Leu Met Leu Asn His Ser Ile Thr Tyr Pro Asp Asn Arg Pro Arg His
                325                 330                 335

Ala Gly Ala Phe Ile Asp Arg Tyr Ile Phe Pro Asp Gly Glu Leu Thr
            340                 345                 350
```

-continued

```
Gly Ser Gly Thr Leu Ile Lys His Met Gln Asp Asn Gly Phe Glu Val
        355                 360                 365

Leu His Glu Glu Asn Leu Arg Phe Asp Tyr Gln Arg Thr Leu His Ala
        370                 375                 380

Trp Cys Glu Asn Leu Lys Glu Asn Trp Glu Glu Ala Val Glu Leu Ala
385                 390                 395                 400

Gly Glu Pro Thr Ala Arg Leu Phe Gly Leu Tyr Met Ala Gly Ser Glu
                405                 410                 415

Trp Gly Phe Ala His Asn Ile Val Gln Leu His Gln Val Leu Gly Val
                420                 425                 430

Lys Leu Asp Glu Gln Gly Ser Arg Gly Glu Val Pro Glu Arg Met Trp
        435                 440                 445

Trp Thr Ile
    450

<210> SEQ ID NO 3
<211> LENGTH: 33
<212> TYPE: DNA
<213> ORGANISM: Corynebacterium glutamicum

<400> SEQUENCE: 3
tgctctagaa aagcaggtgg gaaatgggac agt                                33

<210> SEQ ID NO 4
<211> LENGTH: 33
<212> TYPE: DNA
<213> ORGANISM: Corynebacterium glutamicum

<400> SEQUENCE: 4
tgctctagat ggcagagcta ggcggacata aat                                33
```